United States Patent
Theno

(10) Patent No.: US 7,390,935 B1
(45) Date of Patent: Jun. 24, 2008

(54) HYDROGEL VAPOR DISPENSER

(75) Inventor: Mark H. Theno, Minnetonka, MN (US)

(73) Assignee: Ideagen Incorporated, Minnetonka, MN (US)

( * ) Notice: Subject to any disclaimer, the term of this patent is extended or adjusted under 35 U.S.C. 154(b) by 0 days.

(21) Appl. No.: 09/691,896

(22) Filed: Oct. 19, 2000

(51) Int. Cl.
- *A61F 13/00* (2006.01)
- *A61F 15/00* (2006.01)
- *A61F 13/02* (2006.01)
- *A61K 8/02* (2006.01)
- *A61L 15/16* (2006.01)

(52) U.S. Cl. .......................... 602/58; 424/401; 424/448

(58) Field of Classification Search ................ 424/401, 424/446, 448, 449, 443, 487, 78.02; 514/944, 514/957, 965; 602/58
See application file for complete search history.

(56) References Cited

U.S. PATENT DOCUMENTS

| | | | | |
|---|---|---|---|---|
| 3,318,769 A | * | 5/1967 | Folekemer et al. | 514/144 |
| 5,139,786 A | * | 8/1992 | Ferrini et al. | 424/449 |
| 5,455,043 A | * | 10/1995 | Fischel-Ghodsian | 424/448 |
| 5,501,661 A | * | 3/1996 | Cartmell et al. | 602/58 |
| 5,533,499 A | * | 7/1996 | Johnson | 128/200.24 |
| 5,593,395 A | * | 1/1997 | Martz | 604/304 |
| 5,899,856 A | * | 5/1999 | Schoendorfer et al. | 600/362 |
| 6,010,715 A | * | 1/2000 | Wick et al. | 424/448 |
| 6,033,684 A | * | 3/2000 | Norcia et al. | 424/448 |
| 6,068,853 A | * | 5/2000 | Giannos et al. | 424/449 |
| 6,086,904 A | * | 7/2000 | Crawford | 424/405 |
| 6,244,265 B1 | * | 6/2001 | Cronk et al. | 128/200.24 |
| 6,296,869 B1 | * | 10/2001 | Crotty et al. | 424/448 |
| 6,399,091 B1 | * | 6/2002 | Berthold et al. | 424/443 |

FOREIGN PATENT DOCUMENTS

| | | | | |
|---|---|---|---|---|
| EP | 0123456 A2 | * | 1/2000 | 100/100 |
| ES | 2137528 | * | 12/1999 | |

* cited by examiner

*Primary Examiner*—Sreeni Padmanabhan
*Assistant Examiner*—Yong S. Chong
(74) *Attorney, Agent, or Firm*—Schwegman, Lundberg, & Woessner P.A.

(57) ABSTRACT

The present invention includes a patch. The patch includes a main body with a base portion and a vapor emitting portion. The base portion includes a hydrogel comprising a first surface and an opposing surface. The vapor emitting portion is attached to the first surface of the hydrogel. A vapor emitting material is incorporated in the vapor emitting portion.

33 Claims, 3 Drawing Sheets

HYDROGEL VAPOR DISPENSER

BACKGROUND OF THE INVENTION

The present invention relates to a patch device for emitting vapor and to a method for releasing vapor.

Human beings have been using products that emit scents and aromas since ancient times. These products have been used for purposes such as masking unpleasant odors, attracting a member of the opposite sex, repelling animals and insects, and treating disease symptoms.

In order to extend the time of aroma emission, individuals making and using these products have dissolved or suspended the scents and aromas with other materials. For instance, perfumes are blended with volatiles that control and extend the period of evaporation of a particular scent. The Lindauer U.S. Pat. No. 5,234,689 issuing Aug. 10, 1993, describes a liquid perfume substance. This substance is applied to many areas of the skin. The fragrance is typically in a bottle or flask. Consequently, the user must reapply the substance.

Other formulations capture the aroma or scent material in a solid or a gel matrix. One type of solid matrix is wax in a candle. Scents and aromas within the wax are released when heated. The Nakatsu U.S. Pat. No. 6,086,644 issuing Jul. 11, 2000, describes a scented candle. In order to emit fragrances the candle must be lit. This type of scent emission has only limited use. For instance, the candles are not transportable because of their predisposition to start fires.

Other formulations use polymeric matrices to control release of a scent or aroma. For instance, the Wick U.S. Pat. No. 6,010,715 issuing Jan. 4, 2000, describes a patch for controlled release of a substance. The patch includes a formulation of an active agent and a thermoplastic resin. The formulation releases active agents through the skin. The patch is strategically positioned in order to be effective. Agents released by this patch are limited to substances that are absorbable into the human body.

SUMMARY OF THE INVENTION

One embodiment of the present invention includes a patch that comprises a main body. The main body includes a hydrogel base portion and a vapor emitting portion attached to the hydrogel base portion. A vapor emitting material is incorporated into the vapor emitting portion.

Another embodiment of the present invention includes a vapor emitting patch that includes a hydrogel and a releasable layer that is reversibly adhered to the hydrogel. A pad with a vapor emitting material incorporated into pad, is attached to the hydrogel.

One other embodiment of the present invention includes a vapor emitting patch that includes a couple of layers and a pad attached to one of the layers. The patch includes a first vapor emitting material embedded in a first portion of the pad and a second vapor emitting material embedded in a second portion of the pad.

Another embodiment of the present invention includes a kit comprising vapor emitting patches. The patches are enclosed in packaging.

The present invention also includes a method for releasing a vapor. The method includes providing a patch comprising an adhesive comprising a first surface and an opposing surface, a base substrate adhered to the opposing surface of the adhesive, and a vapor emitting portion affixed to the first surface of the adhesive. The method also includes exposing the pad to air. The method further includes releasing the vapor.

DETAILED DESCRIPTION

Figure 1:
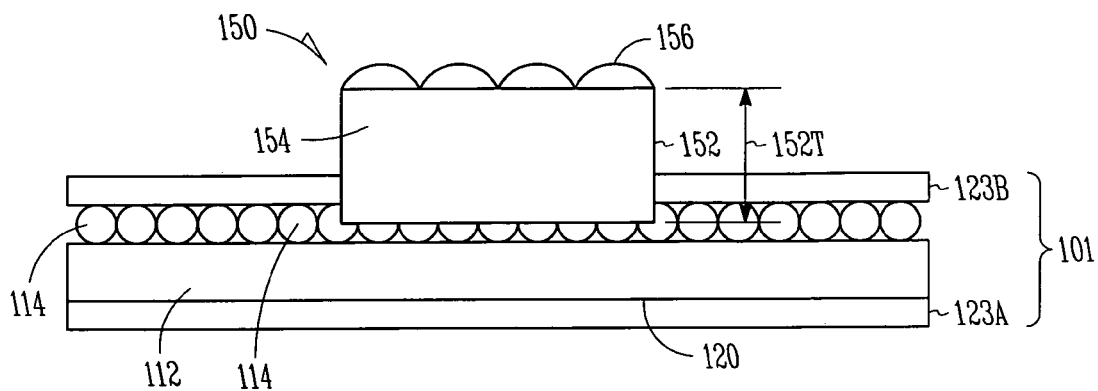
FIG. 1 is a cross-sectional view of a patch of the present invention.

The vapor emitting patch of the present invention, one embodiment of which is illustrated generally at 100 in Fig., includes a main body 10 that comprises a base portion 101 and a vapor emitting portion 150, wherein the vapor emitting portion 150 is affixed to the base portion 101 by an adhesive 114. The base portion comprises a hydrogel base substrate 120, and releases layers 123a and 123b that releasably expose the hydrogel base substrate 120. The vapor emitting portion 150 includes a cellular main body 152 and a protective mesh 156 that overlays the cellular main body 152. Vapor emitting substances are incorporated within the cellular main body 152.

For some embodiments, the vapor emitting portion 150 comprises an open cellular pad 152 that incorporates a vapor emitting material 154, and, for some embodiments, a mesh or netting 156 positioned on a top surface of the open cellular pad 152. Vapor emitting materials 154 usable in the present invention include a variety of materials that emit vapors at ambient temperatures and pressures, such as perfumes, drugs, and pheromones.

The patch 100 is attachable to skin and non-living materials by an adhesion of the hydrogel base portion 120 to skin and to other non-living surfaces once the release layer 123a is removed. For some use embodiments, the patch 100 is adhered to a surface once the release layer 123b is removed.

The patch 100 transportable. The shape and structure of the patch 100 are adaptable for use in a variety of environments. The patch 100 may be positioned so that the vapor emitting portion 150 is positioned either outward into an environment or inward, facing a surface.

The patch of the present invention 100 comprises at least one reservoir of vapor emitting material. For some embodiments, the vapor emitting portion includes many cells for receiving a vapor emitting substance. The vapor emitting material may be the sole material in the reservoir or, for some embodiments, the reservoir may include a blend or mixture of vapor emitting material and other liquid or gel materials. The other materials act as carriers that orchestrate release of scents. For instance, one vapor emitting substance is incorporated in a carrier with a very high vapor pressure and another vapor emitting substance is incorporated in a carrier with a very low vapor pressure. For some embodiments, the same vapor emitting substance is incorporated in carriers having a spectrum of vapor pressures. The use of a spectrum of carriers along with an incorporation in a large number of air cells prolongs the release of a substantially constant quantity of vapor. For some embodiments, it is a single vapor that is released. For other embodiments, two or more vapors are sequentially released or, for other embodiments, concurrently released.

By using the patch 100, an individual senses a scent or aroma that is continuously released for a prolonged period of time. By using the patch 100, the user does not have to apply the vapor emitting material repeatedly to the skin or a user. This is an improvement over a lotion or spray wherein vapor emitting material is rapidly released and must be frequently reapplied.

The patch 100 is manufactured, for a variety of embodiments, with materials having various colors. The patch 100 may be flesh colored so as not to be readily seen. The patch 100 may be made with a bright vibrant color to attract attention. The patch 100 may also be made in a wide variety of sizes and shapes, depending upon the application.

Embodiments of the patch 100 are fabricated to accommodate many different uses. For instance, a patch incorporating an animal scent is usable by a hunter. The hunter may wear the patch 100 or may affix the patch 100 to a surface. The purpose of this type of patch is to attract an animal.

Figure 8:
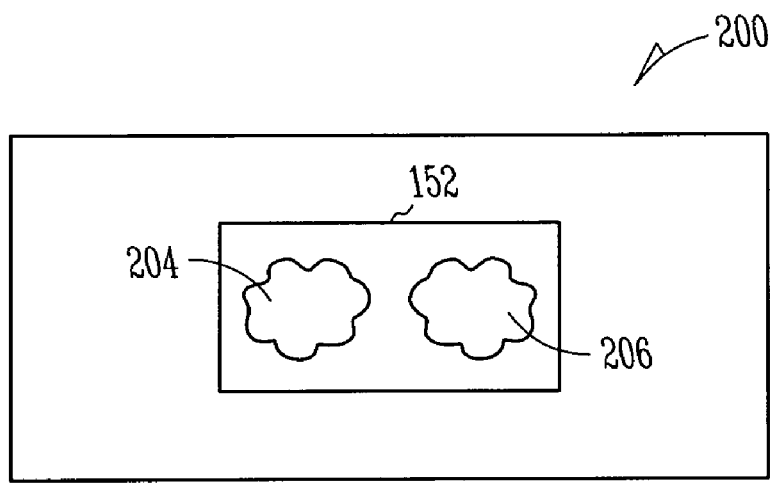
FIG. 8 is a top plan view of a pad embodiment that incorporates two scents.

A patch incorporating both an animal scent and an insect repellent is also usable. For this embodiment, the cellular pad 152 incorporates a solution or mixture of an animal scent and insect repellent. These scents are concurrently released. In another embodiment, the patch 100 comprises a cellular pad 152 with an animal scent 204 localized in one portion of the pad and an insect repellent 206 localized in another portion of the pad. This embodiment is illustrated at 200 in FIG. 8.

In another embodiment, the patch 100 incorporates a cosmetic fragrance, such as a perfume or cologne. The patch embodiment may be affixed to the body of a user in a location that is hidden from view. This patch embodiment permits a user to have the benefits of a fragrance without detrimental effects, such as a staining of clothing, as is caused by oil based scents. This embodiment also provides the user with a longer period of vapor releasing effectiveness.

Some embodiments of the patch incorporate a medicinal vapor emitting material. For example, if vapor rub menthol gel is the substance incorporated, the patch 100 is usable to relieve coughing and congestion. For this embodiment, the patch 100 is generally applied to part of a human body. Other medicinal vapor emitting materials embedded in the pad to treat a wide range of ailments include aroma therapy products. These are only some of the uses of the patch 100. A wide variety of vapor emitting materials can be stored in the vapor emitting portion.

Active agents include psychoactive agents such as nicotine, caffeine, mesocarb, mefexamide, cannabinols, such as THC and the like; sedatives such as deazepam, mepiridine, uldazepam, tybamate, and metaclazepam; and antibiotics such as tetracycline and penicillin.

Figure 6:
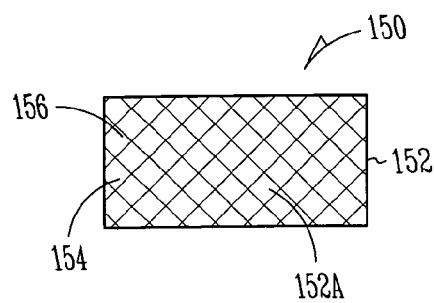
FIG. 6 is a top view of the top surface of the pad.
Figure 7:
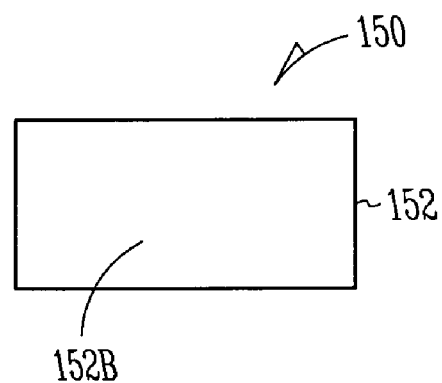
FIG. 7 is a back view of the bottom surface of the pad.

For some embodiments, vapor emitting material 154 is located on the top surface 152a of the cellular pad 152, as shown in the top view of vapor emitting portion in FIG. 6.

A kit embodiment of the present invention, illustrated generally at 300 in FIG. 9 includes a package 302 and the patch 100, which is enclosed within the package. When the patch 100 is removed from the package 302, and the pad 152 of the patch 100 is exposed to air, the vapor emitting material 154 is released into the air. The vapor emitting material 154 includes materials such as perfume, cologne, animal scents, insect repellants, vapor rub menthol gel, aroma therapy, and many others.

The cellular foam pad 152 receives, retains, and releases vapor emitting material 154. The cellular structure of the pad permits a gradual and substantially constant release of vapor emitting material. In particular, cells within the pad 152 store the vapor emitting material 154 and release vapor in accordance with the local vapor pressure within the cellular structure of the pad and at the interface of the pad 152 and atmosphere.

In one embodiment, the pad 152 is made from a synthetic foam material. Other pad materials include natural foam or other foam materials. It is believed that open cellular structures are generally usable. The open cellular structures are made of materials such as polyolefins, acrylic adhesives as well as hydrogels. In one embodiment, the pad 152 is rectangularly shaped. In other embodiments, the pad 152 comprises shapes, such as circular, triangular, oval, and hexagonal shapes. In one embodiment, the pad 152 has a thickness 152t of about 0.4 centimeters and is located in the center of film layer 112. In other embodiments, the pad 152 can have a thickness 152t of about less than 0.1 centimeters, less than about 1.0 centimeter, less than about 5.0 centimeters, or less than about 10.0 centimeters. Some embodiments of the pad 152 omit one or more of these features. Thus, the pad 152 is not limited to any particular dimensional selection, location, color, or composition. Embodiments of the patch have a capability to be very thin.

Figure 3:
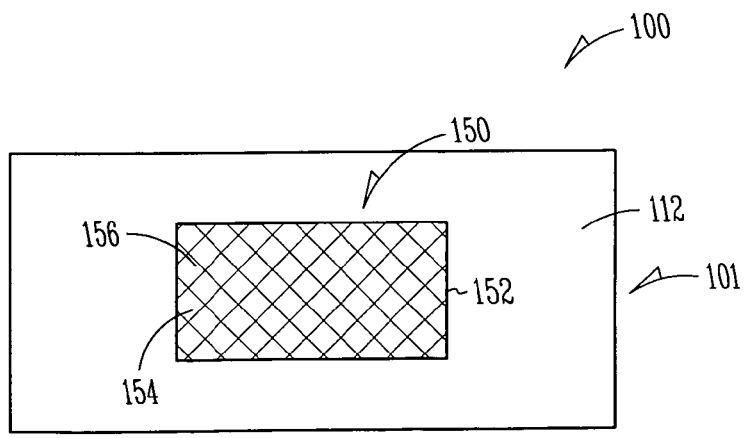
FIG. 3 is a top view of the patch of the present invention.

In one embodiment the protective member 156 is a netting material that is ultrasonically sealed to the pad 152. In other embodiments the protective member 156 is formed from materials such as mesh or scrim and is attached to the pad 152 by other mechanisms. The protective member 156 does not cover the entire top surface 152a of the pad 152, and thus allows the vapor emitting material 154 to be released into the air. The protective member 156 prevents objects from coming into contact with the pad 152, where the vapor emitting material 154 is located, as illustrated in the top view of the patch 100 in FIG. 3. The protective material 156 is not limited to any particular material, size, shape or color.

The base portion 101 comprises the release layer 123b, the hydrogel 114, and the release layer 123a. The vapor emitting portion 150 is affixed to the base portion 101, which is used to attach the patch 100 to skin and non-living materials. Some embodiments omit one or more of the release layers 123a and 123b.

Figure 2:
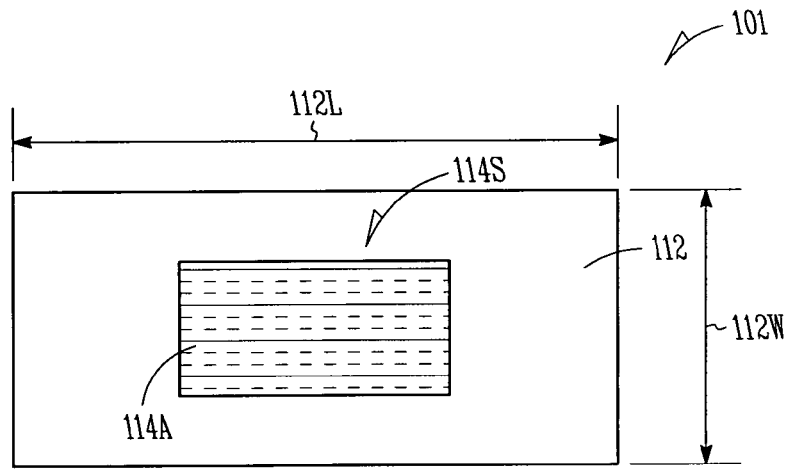
FIG. 2 is a top view of the base portion.

The release layer 123b is affixed to a first surface 114a of the hydrogel. The release layer 173b allows the pad 152 to be attached directly to the first surface 114a of the hydrogel 114 while also protecting the first surface 114a of the hydrogel 114 from adhering to any undesirable object. In one embodiment, the release layer 123a is fabricated to form a rectangular shaped piece of film. A portion of the release layer 123b is removed, and therefore an area of the first surface 114a of the hydrogel 114 is not covered by the film layer 123b, as shown in the top view of the base portion in FIG. 2. This area is the adhesive section 114s. The portion of the film layer is removed in order to affix the pad 152 directly to the adhesive 114, as shown in FIG. 1.

In various embodiments the release layers 123a and 123b include polyolefins, polyamides, polyethylene terephthalates, cellulose, paper, foil or any combination thereof. In one embodiment the film layer 123b has a length 112l of about 7.0 centimeters and a width 112w of about 6.0 centimeters. However, in other embodiments the film layer 173b can have a length or width of about less than 1.0 centimeter, less than about 10.0 centimeters, less than about 25.0 centimeters, or less than about 100.0 centimeters. The film layer 123a is not limited to any particular material, size, shape, or color.

The hydrogel 114 is attachable to skin and can also be attached to non-living materials such as a wall, a window, a desk, a refrigerator, a car, a bag, and many others, once the release layer 123a or 123b is removed.

Figure 4:
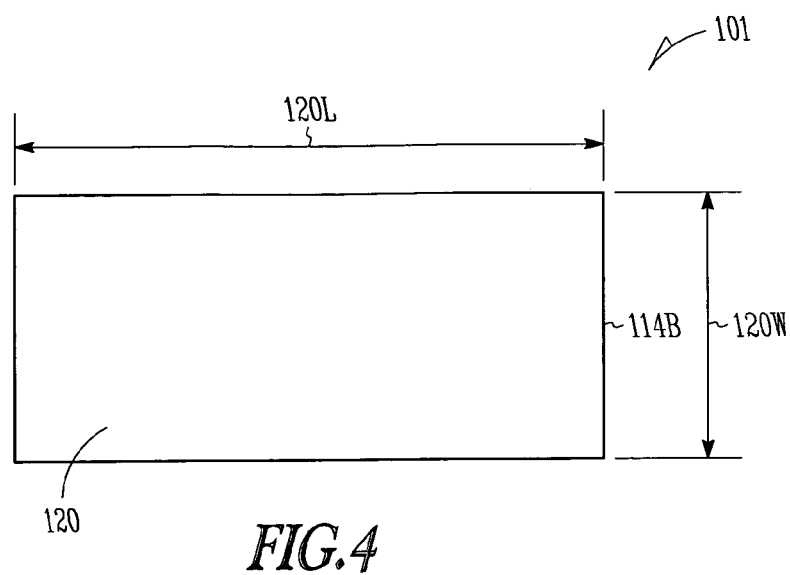
FIG. 4 is a view of the back side of a patch with the base substrate attached to the patch, wherein the base substrate is partially detached from the patch.
Figure 5:
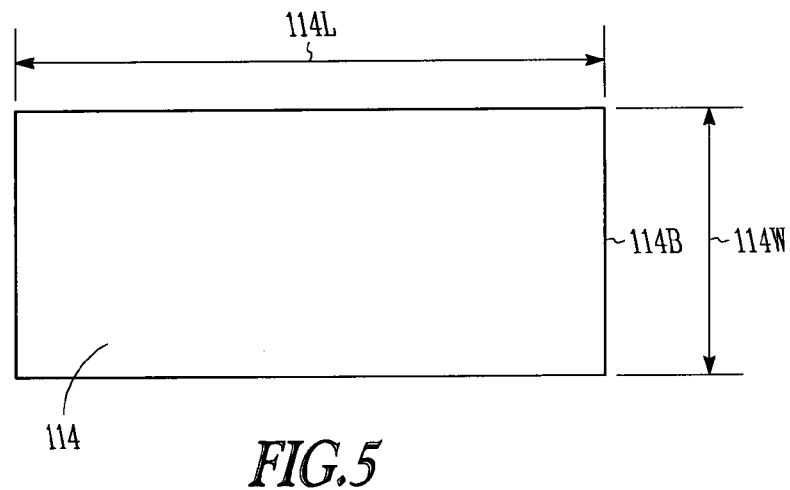
FIG. 5 is a back view of the opposing surface of the adhesive.

The release layers 123a and 123b are attached directly to the hydrogel 114, as shown in the cross-sectional view of FIG. 4. The release layers 123a and 123b prevent the opposing surface 114b of the adhesive 114 from being attached to a surface prior to its intended use. The release layers 123a and 123b are removable and flexible. Once the patch 100 is ready to be used, the release layer 123a or 123b is removed from the hydrogel. If desired, the release layer 123a and 123b is reattached to the opposing surface 114b of the hydrogel 114, once removed.

The release layers 123a and 123b are typically made of any suitable material that is flexible, easily removed, and that can be attached and reattached to the opposing surface 114b of the adhesive 114.

In one embodiment the release layer 123a has a length 120l of about 7.0 centimeters and a width 120w of about 6.0 centimeters. However, in other embodiments the release layer 123a has a length or width of about less than 1.0 centimeter, less than about 10.0 centimeters, less than about 25.0 centimeters, or less than about 100.0 centimeters. The release layer 123a is not limited to any size, shape, or color.

The illustrative patch 100 and other patches can be made using several techniques. One method of making the patch is to cut a piece of the hydrogel 114 in the shape desired for the patch 100. The hydrogel 114 can be cut using a scalpel, a knife, a machine with a cutting device, or any other suitable cutting device. Next, a piece of a pad 152 is cut into the desired size. Then, a piece of film 112 is cut in the same shape as the hydrogel 114 using a scalpel, a knife, a machine with a cutting device, or any other suitable apparatus for cutting film. The pad 152 is then placed on top of the release layer 123b for sizing. An area equivalent to the perimeter of the pad 152 is cut out of the release layer 123b. The release layer 123b is adhered to the hydrogel 114. The area where the film was cut out exposes the hydrogel 114. The exposed hydrogel 114 allows the pad 152 to be affixed directly to the hydrogel 114. The patch 100 is mass producible using conventional manufacturing techniques.

The release layers 123a and 123b are also cut into the same shape as the hydrogel 114. The release layers 123a and 123b are adhered to the hydrogel 114. Vapor emitting material is added to the pad or foam material of the vapor emitting portion 150. Then, the protective material 156 is cut into the same shape as the pad or foam material 152. The protective material 156 is then ultrasonically sealed to the top surface 152a of the pad 152. The pad 152 is then affixed directly to the hydrogel 114 by placing it directly on the adhesive section 114s, the exposed area of the hydrogel 114 where the release layer 123b that has been cut out.

Finally, the patch 100 is placed in packaging. For some embodiments, the packaging comprises a plastic sealed bag or a box that contains one patch. The patches are, for some embodiments, wrapped individually or with other patches. The patches are, for other embodiments, packaged in a kit with other devices. For example, a kit can contain a patch without the vapor emitting material 154 and a separate bottle or container with either one or more vapor emitting materials 154.

The preceding detailed description, which references and incorporates FIG. 1-8, describes and illustrates one or more specific embodiments of the invention. These embodiments, offered not to limit but only to exemplify and teach the invention, are shown and described in sufficient detail to enable those skilled in the art to practice the invention. Thus, where appropriate to avoid obscuring the invention, the description may omit certain information known to those skilled in the art.

What is claimed is:

1. A vapor emitting patch comprising:
    a base portion comprising a hydrogel;
    a cellular structure, comprising a foamed polyolefin, contacting the base portion, the cellular structure comprising a vapor emitting portion; and
    a vapor emitting material that is a drug stored within the vapor emitting portion.

2. The patch of claim 1 wherein the base portion further comprises a film layer wherein the film layer reversibly adheres to the hydrogel.

3. The patch of claim 2 wherein the film layer is removable.

4. The patch of claim 1 wherein the vapor emitting portion comprises a pad.

5. The patch of claim 4 wherein the pad comprises a material selected from the group of materials consisting of polyolefins, acrylic adhesives and hydrogels.

6. The patch of claim 4 wherein the vapor emitting portion comprises a protective material that overlays the pad.

7. The patch of claim 6 wherein the protective material comprises a mesh material or a non-woven material.

8. A patch comprising:
    a hydrogel comprising a first surface and an opposing surface;
    a releasable layer adhered to the hydrogel;
    a foam pad comprising a cellular structure comprising foamed polyolefin, the pad comprising a top surface and a bottom surface wherein the bottom surface of the pad is affixed to the hydrogel; and
    a vapor emitting material selected from the group consisting of drugs, pheromones, and perfumes received by the cells of the foam pad wherein the vapor emitting material is added to the cells prior to use.

9. The patch of claim 8 wherein the pad comprises an open cell foam.

10. The patch of claim 8 and further comprising a protective member sealed to the top surface of the pad.

11. The patch of claim 8 further comprising a layer attached to the hydrogel wherein the layer attached to the hydrogel is a film, a foil or a paper.

12. The patch of claim 11 wherein the film layer comprises a material selected from the group of materials consisting of polyolefins, polyamides, cellulosics, polyethylene terephthalates, or any mixture thereof.

13. A patch comprising:
    an adhesive first layer comprising a first surface and an opposing surface with the surfaces having areas;
    a second layer, comprising a hydrogel, releasably adhered to and covering the entire area of the opposing surface of the first layer;
    a foam pad, comprising a foamed polyolefin, having portions and comprising a top surface and a bottom surface with one of the pad surfaces attached to and covering an area of the first surface of the first layer; and
    at least two vapor emitting materials separately stored in at least two separate portions of the pad.

14. The patch of claim 13 further comprising a third layer wherein the third layer is releasably affixed to and covers the uncovered areas of the first surface of the first layer.

15. The patch of claim 13 further comprising a protective layer wherein the protective layer is attached to the top surface of the pad.

16. The patch of claim 13 wherein the first layer comprises an adhesive from which a release layer can be released.

17. The patch of claim 16 wherein the adhesive comprises a hydrogel.

18. The patch of claim 14 wherein the third layer is a film, a foil or a paper.

19. The patch of claim 18 wherein the film comprises a material selected from the group consisting of polyolefins, polyamides, cellulosics, polyethylene terephthalates, or any mixture thereof.

20. The patch of claim 13 wherein the second layer comprises a removable and reattachable base substrate.

21. The patch of claim 13 wherein the pad comprises a synthetic or natural open cell foam.

22. A method for releasing a vapor, comprising:
providing a patch comprising
an adhesive comprising a first surface and an opposing surface,
a base substrate, comprising a hydrogel, adhered to the opposing surface of the adhesive,
a cellular structure, comprising a foamed polyolefin, contacting the base portion, the cellular structure comprising a vapor emitting portion; and
a vapor emitting material selected from the group consisting of drugs, pheromones, and perfumes stored within the cellular structure;
removing the base substrate;
attaching the adhesive to a surface;
exposing the pad to air; and
releasing the vapor.

23. The method of claim 22 wherein attaching the adhesive to a surface comprises attaching the adhesive to skin.

24. The method of claim 22 wherein removing the base substrate comprises removing the base substrate from the opposing surface of the adhesive.

25. The method of claim 22 wherein exposing the pad to air includes removing the patch from a packaging.

26. A method for releasing a vapor comprising:
providing a patch comprising:
an adhesive comprising a first surface and an opposing surface,
a base substrate, comprising a hydrogel, adhered to the opposing surface of the adhesive, and
a vapor emitting portion comprising a cellular structure, comprising foamed poyolefin, and a vapor emitting material stored within the cellular structure comprising the vapor emitting portion affixed to the first surface of the adhesive;
exposing the pad to air; and
releasing the vapor.

27. The method of claim 26 wherein providing a patch includes removing the base substrate and attaching the adhesive to a surface.

28. The method of claim 26 wherein exposing the pad to air includes removing the patch from a packaging.

29. A kit for releasing a vapor comprising:
one or more patches comprising a hydrogel and a vapor emitting portion comprising a cellular structure comprising a foamed polyolefin, and a vapor emitting material stored within the cellular structure comprising the vapor emitting portion, with the vapor emitting portion adhered to the hydrogel; and
a container for enclosing the patches.

30. The kit of claim 29 and further comprising a container for enclosing more than one patch.

31. A vapor emitting patch comprising:
a base portion comprising a hydrogel;
a cellular structure, comprising a foamed polyolefin, contacting the base portion, the cellular structure comprising a vapor emitting portion; and
a vapor emitting material that is a pheromone stored within the vapor emitting portion.

32. A vapor emitting patch comprising:
a base portion comprising a hydrogel;
a cellular structure, comprising a foamed polyolefin, contacting the base portion, the cellular structure comprising a vapor emitting portion; and
a vapor emitting material that is a perfume stored within the vapor emitting portion.

33. A vapor emitting patch comprising:
a base portion comprising a hydrogel;
a cellular structure, comprising a foamed polyolefin, contacting the base portion, the cellular structure comprising a vapor emitting portion; and
a vapor emitting material having a low vapor pressure stored within the vapor emitting portion.

* * * * *

UNITED STATES PATENT AND TRADEMARK OFFICE
CERTIFICATE OF CORRECTION

| | | |
|---|---|---|
| PATENT NO. | : 7,390,935 B1 | Page 1 of 1 |
| APPLICATION NO. | : 09/691896 | |
| DATED | : June 24, 2008 | |
| INVENTOR(S) | : Theno | |

It is certified that error appears in the above-identified patent and that said Letters Patent is hereby corrected as shown below:

In column 2, line 22, delete "Fig.," and insert -- Fig. 1, --, therefor.

In column 3, line 50, delete "deazepam," and insert -- diazepam, --, therefor.

In column 3, line 50, delete "mepiridine," and insert -- meperidine, --, therefor.

In column 5, line 63, delete "FIG." and insert -- FIGS. --, therefor.

In column 7, line 1, in Claim 17, after "comprises" insert -- one or more of a hydrocolloid, polysaccharide and --.

In column 7, line 14, in Claim 22, after "comprising" insert -- : --.

In column 7, line 43, in Claim 26, delete "poyolefin," and insert -- polyolefin, --, therefor.

Signed and Sealed this

Eleventh Day of May, 2010

David J. Kappos
*Director of the United States Patent and Trademark Office*